United States Patent [19]
Dubief et al.

[11] Patent Number: 5,824,296
[45] Date of Patent: Oct. 20, 1998

[54] SOLID HAIR COMPOSITION CONTAINING A PARTICULAR STRUCTURING AGENT

[75] Inventors: Claude Dubief, Le Chesnay; Arnaud De Labbey, Aulnay-Sous-Bois; Roland De La Mettrie, Le Vestinet; Christine Rondeau, Sartrouville, all of France

[73] Assignee: L'Oreal, Paris, France

[21] Appl. No.: 500,752

[22] Filed: Jul. 11, 1995

[30] Foreign Application Priority Data

Jul. 11, 1994 [FR] France .................................. 94 08567

[51] Int. Cl.$^6$ ...................................................... A61K 7/00
[52] U.S. Cl. ...................... 424/70.11; 424/70.1; 424/70.5
[58] Field of Search ............................... 424/70.11, 70.7, 424/62, 63, 489, 501, 401, 69, 70.6, 78.03, 70.5, 70.1, 70.19; 510/119; 8/405

[56] References Cited

U.S. PATENT DOCUMENTS

| | | | |
|---|---|---|---|
| 4,155,870 | 5/1979 | Jorgensen | 252/131 |
| 5,053,221 | 10/1991 | Robertson et al. | 424/63 |
| 5,496,543 | 3/1996 | Lagrange et al. | 424/70.7 |
| 5,510,107 | 4/1996 | Lecomte et al. | 424/401 |
| 5,679,326 | 10/1997 | Bara et al. | 424/70.1 |

FOREIGN PATENT DOCUMENTS

| | | |
|---|---|---|
| 652391 | 5/1992 | Australia . |
| A-214626 | 3/1987 | European Pat. Off. . |
| A-287773 | 10/1988 | European Pat. Off. . |
| A-295903 | 12/1988 | European Pat. Off. . |
| A-348015 | 12/1989 | European Pat. Off. . |
| A-379409 | 7/1990 | European Pat. Off. . |
| A-486394 | 5/1992 | European Pat. Off. . |
| WO-A-9414402 | 7/1994 | WIPO . |

OTHER PUBLICATIONS

Kirk—Othmer, Encyclopedia of Chemical Technology, 3rd Edition. John Wiley & Sons, N.Y. vol. 21, pp. 106–131. (1983). Size Measurement of Particles.

*Primary Examiner*—Robert H. Harrison
*Attorney, Agent, or Firm*—Oblon, Spivak, McClelland, Maier & Neustadt, P.C.

[57] ABSTRACT

The invention relates to a hair composition containing, in a cosmetically acceptable medium, a structuring agent insoluble in this medium and formed of solid particles, which imparts a deformable solid appearance to the composition in which the medium is contained, this agent being capable of being removed from the hair using a diluent. This composition may be a shampoo, a conditioner, a composition for dyeing or bleaching keratin fibers or alternatively a composition for permanent-waving or straightening keratin fibers.

17 Claims, No Drawings

SOLID HAIR COMPOSITION CONTAINING A PARTICULAR STRUCTURING AGENT

BACKGROUND OF THE INVENTION

1. Field of the Invention

The present invention relates to a novel hair composition of deformable solid appearance. This hair composition may consist of a shampoo, a conditioner, a composition for dyeing or bleaching keratin fibers or alternatively a composition for permanent-waving or straightening these fibers. The invention applies more especially to treatments of human hair, eyelashes or eyebrows.

The invention also relates to a process for the cosmetic treatment of keratin fibers, to a process for dyeing, bleaching, permanent-waving, washing and/or conditioning keratin fibers and to a process for delivering a specific active agent onto keratin fibers.

The invention further relates to the use of a specific structuring agent in a hair composition.

2. Discussion of the Background

Hair compositions are usually in the form of liquids or creams that are viscous to a greater or lesser extent. The more liquid the compositions, the harder it is to hold them in the hands and the harder it is to measure them out. The reason for this in that these compositions tend to escape through the fingers. Moreover, the more liquid these compositions, the more liable they are to escape from their packaging.

In a simplified manner, a hair composition comprises one or more active agents such as detergents, dyes, conditioning and permanent-waving active agents, in a cosmetically acceptable support or medium containing a large amount of water and usually surface-active agents.

After each specific hair treatment (shampooing, permanent-waving, dyeing, etc.), it is generally necessary to rinse the hair in order for only the treating active agents (conditioner, dye) to remain upon it and in order to remove the support and especially the surface-active agents. Unfortunately, a large number of hair compositions have the drawback of being difficult to rinse out, that is to say of taking a long time to rinse out, and/or of leaving traces of product on the hair, impart a sticky, waxy, tacky appearance thereto in particular.

Moreover, users are increasingly seeking novel product textures and new product concepts.

The subject of the present invention is, indeed, a novel hair composition which makes it possible in particular to overcome the drawbacks mentioned above. In particular, this composition in rinsed out in a noteworthy manner and has a quite uncommon texture. In addition, it is simple to apply.

The term "hair" should be understood equally to mean hair, eyelashes and eyebrows.

The Applicant has found, surprisingly, that it was possible to impart a deformable solid appearance to a hair composition by using a novel structuring or texturing agent.

SUMMARY OF THE INVENTION

Thus, the invention relates to a hair composition, comprising, in a cosmetically acceptable medium, 1) an active agent; and ii) a structuring agent insoluble in said medium and formed of solid particles, which imparts a deformable solid appearance to said composition in which said medium is contained, said structuring agent being capable of being removed from hair using a diluent.

Another object of the invention is the use of a structuring agent in a hair composition in order to impart a deformable solid appearance thereto, this agent being formed of solid particles and being capable of being removed using a diluent.

According to the invention, the structuring agent may be formed of one or more types of particles.

One of the advantages of this solid texture is that there in no risk of the composition of the invention escaping from its packaging, especially during transport. Moreover, this composition in very easy to handle and does not run between the fingers. It is much easier to measure out than liquid compositions.

Another advantage of this texture is an excellent comfort on application. In particular, the composition does not run at all, in contrast with conventional compositions, which run the risk of irritating the face and the eyes in particular. The absence of running in very much appreciated in the case of permanent-waving and dyeing operations, as well as for shampoos intended for children.

DETAILED DESCRIPTION OF THE PREFERRED EMBODIMENTS

According to the invention, the composition is of a dry, deformable solid appearance, does not stain and resembles marshmallow (see document U.S. Pat. No. 3,682,659 for the consistency of marshmallow). This solid may be modelled like children's plasticine. It may be broken readily by hand so as to take only the required amount of product. In particular, this composition may be packaged in single-dose form and, for example, in the form of small cubes or in sachet form.

By virtue of the particles of the invention, it is possible in particular to obtain a homogeneous (deformable solid) structure for constituents which normally lead to two separate phases (immiscible constituents, for example oil/water).

For the purpose of obtaining a solid which feels soft and pleasant, it is preferable to use particles having a mean particle size of from 1 $\mu$m to 300 $\mu$m, preferably from 5 $\mu$m to 200 $\mu$m, more preferably from 10 $\mu$m to 100 $\mu$m and most preferably from 15 $\mu$m to 40 $\mu$m.

In order to impart a light and airy appearance to the composition of the invention, particles having a density of less than 0.09 kg/cm$^3$ and better still of less than 0.06 kg/cm$^3$ and even better still of less than 0.04 kg/cm$^3$ are advantageously used.

For the purpose of obtaining this low density, hollow particles filled with a gas are advantageously used. Specific non-limiting examples of such a gas includes air, nitrogen, isobutane, isopentane, carbon dioxide, chlorofluorocarbons or hydrochlorofluorocarbons etc.

According to another advantageous characteristic of the invention, the particles are in the form of beads. It is, however, possible to use particles in the form of fibers or needles.

These particles may be made of various inert materials which do not react chemically with the cosmetically acceptable medium or support; in particular, these particles do not react with the oils, the surfactants, the water and the various other constituents of the composition, such as the active agents.

The structuring agent of the invention has the particular feature of being readily removed from the hair by a simple dilution. It acts, in fact, as a vehicle or reservoir for the cosmetic support. It moreover enables the support and especially the active agent or agents, contained in the deformable solid, to be recovered, when necessary, by simple dilution with water. This is probably due to the fact that the cosmetic support is housed in the interparticulate spaces of the solid and not encapsulated in the particles.

Besides water, water to which one or more cosmetically acceptable polar solvents such an lower $C_{1-5}$ alcohols (isopropanol or ethanol) and propylene glycol has been added, and to which one or more surfactants has been added, may be used as diluent. Salt-charged water may also be used.

As a selection criterion for a structuring agent, the following test may be performed:
addition of determined particles in water containing a dye conventionally used in the hair field, such as HC Blue 2, until a colored paste is obtained,
pouring of a drop of water onto the paste.

When the paste is much clearer at the point of impact of the drop of water than the rest of the paste, this means that the particles in question may be suitable as a structuring agent. On the other hand, when the paste is not decolorized at the point of impact, the particles in question are not at all suitable.

The inert particles are advantageously made of glass or of thermoplastic materials, for instance polyamides such as nylon, polymers or copolymers of acrylonitrile, of vinylidene chloride, of vinyl chloride and/or of acrylic or styrene monomer, which may be expanded. The acrylic monomer is, for example, a methyl or ethyl acrylate or methacrylate. The styrene monomer is, for example, α-methylstyrene or styrene.

As glass particles which may be used in the invention, there may be mentioned the hollow glass beads sold by the company 3M under the reference SCOTCHLITE GLASS BUBBLES S 22. 95% of these beads have a diameter of less than 74 μm.

Nylon particles which may be used are the "ORGASOL" particles sold by the company Atochem. These particles are porous solid spheres of diameter ranging from 5 μm to 60 μm.

The particles are preferably hollow deformable particles of an expanded copolymer of vinylidene chloride/acrylonitrile or of vinylidene chloride/acrylonitrile/methacrylate. It is possible, for example, to use a terpolymer containing: from 0% to 60% of units derived from vinylidene chloride, from 20% to 90 of units derived from acrylonitrile and from 0% to 50% of units derived from an acrylic or styrene monomer, the sum of these percentages (by weight) being equal to 100. These particles may be dry or hydrated and are, for example, those sold under the trade name EXPANCEL by the company Nobel Casco and in particular under the references 551 DE 12 (particle size of approximately 12 μm and density of approximately 40 kg/m$^3$), 551 DE 20 (particle size of approximately 30 μm and density of approximately 65 kg/m$^3$), 551 DE 50 (particle size of approximately 40 μm), 461 DE 50 and 642 WE 50 of particle size approximately 50 μm, and 551 DE 80 (particle size of approximately 80 μm).

It is also possible to use particles of this same terpolymer having a particle size of approximately 18 μm and a density of approximately 60 kg/m$^3$ to 80 kg/m$^3$ or alternatively having a particle size of approximately 34 μm and a density of approximately 20 kg/m$^3$.

It is also possible to use particles of a polymer of vinylidene chloride/acrylonitrile or of vinylidene chloride/acrylonitrile/methacrylate which is not expanded, such as those sold under the trade name EXPANCEL with the reference 551 DU 10 (particle size of approximately 10 μm) or 461 DU 15 (particle size of approximately 15 μm).

As other hollow polymer particles which may be used in the invention, there may also be mentioned the polymers and the copolymers obtained from itaconic, citraconic, maleic and fumaric acids or esters and from vinyl acetate or lactate (see in this regard document JP-A-2-112,304).

In contrast, particles of corn starch, pyrogenous silica or of non-expanded polyester, polyurethane or polyethylene do not make it possible to obtain a solid composition which is removed well from the hair during rinsing.

It is, admittedly, known to modify the viscosity of a liquid medium with solid particles (see on this subject the article Elsevier Sequoia, 1992, Progress in Organic Coatings, 21, p. 255–267, from A. Toussaint "Choice of Rheological model for steady flow: application to industrial concentrated suspensions") but nobody to date has either described or suggested the use of the solid product, obtained from a certain concentration of particles, in the hair field in order to store the medium in which the particles are dispersed.

In other words, the production or otherwise of the deformable solid is linked to the amount of structuring agent used in the composition; above a certain quantity of particles, referred to as the critical pigment charge volume and abbreviated to C.P.C.V., a sudden increase in the viscosity of the medium is observed. The C.P.C.V. is a function of the medium and of the nature of the particles; it must thus be determined every time. Its determination poses no problem to those skilled in the art. It is possible, for example, to use the official ASTM method in order to determine the C.P.C.V. Preferably the amount of particles is equal to or greater than the C.P.C.V.

The composition of the invention may consist of a shampoo, a conditioner, a hair shaping product, a permanent-waving agent or a hair straightening agent, or a composition for dyeing or bleaching via a direct route or an oxidation route. According to the specific application envisaged, the composition of the invention may contain at least one active agent chosen from detergents, dyes, permanent-waving agents, polymers and cations.

In the case of oxidation dyeing, the composition of the invention may be packaged in two separate containers each containing a deformable solid, one enclosing the dye composition containing the oxidation dye precursors (base+coupler), the other enclosing the oxidizing agent. These two solids may be mixed together by hand, just before use. The mixture is then applied to wet hair. It in then left to act as for any conventional dye composition, and finally the hair is rinsed.

Moreover, the introduction of these particles into permanent-waving compositions makes it possible to reduce the odor thereof appreciably.

Another subject of the invention is the use of the composition defined above for treating keratin fibers and especially the hair.

The composition of the invention is advantageously applied to wet keratin fibers. It may, however, be used on dry hair, after having previously been diluted with water.

Thus, another subject of the invention is a treatment process for keratin fibers and especially wet keratin fibers, which comprises in applying a composition as defined above to the wet fibers, followed by rinsing said fibers. More especially, the invention also relates to a process for dyeing, bleaching, permanent-waving, washing and/or conditioning keratin fibers, comprises applying to said fibers, in the presence of water, a composition as defined hereinabove, followed by rinsing said fibers.

Another subject of the invention is a process for delivering an active agent onto keratin fibers, consisting in enclosing the active agent in a deformable solid containing a cosmetically acceptable medium and a structuring agent insoluble in this medium, formed of solid particles by applying at least some of the deformable solid to the fibers, in the presence of water, in order to release the active agent into it, and then removing the structuring agent by rinsing the fibers.

The composition of the invention may contain, besides the structuring particles and the active agents, all the constituents conventionally used in hair compositions. These constituents are, in particular, mineral, plant, synthetic or silicone-containing oils, water, alcoholic solvents, screening agents, fragrances, surfactants, polymers, preserving agents, antioxidants, pH regulators, sequestering agents, fillers, etc.

Having generally described this invention, a further understanding can be obtained by reference to certain specific examples which are provided herein for purposes of illustration only and are not intended to be limiting unless otherwise specified clearly. In the examples, AM means active material and EO means moles of ethylene oxide.

EXAMPLE 1

Shampoo

| | |
|---|---|
| Sodium lauryl ether sulphate containing 2.2 EO, sold under the name EMPICOL ESB 3/FG by the company Albright and Wilson at an AM concentration of 28% | 15% AM |
| Cocoylbetaine | 3% AM |
| Polydimethylsiloxane sold under the name SILBIONE OIL 70 047V500000 by the company Rhône Poulenc | 2.7% |
| Sodium chloride | 11% |
| SCOTCHLITE GLASS BUBBLES S22 from the company 3M (hollow glass spheres) | 25% |
| Preserving agent, fragrance | qs |
| Water | qs 100% |
| pH adjusted with HCl to | 8 |

A smooth white paste which is easily modellable, is easy to apply and rinses off satisfactorily is obtained.

COMPARATIVE EXAMPLE 1

Shampoo

| | |
|---|---|
| Lauryl ether sulphate of sodium and of magnesium 80/20 containing 4 mol EO, sold under the name EMPICOL BSD by Albright and Wilson | 6% AM |
| Alkyl polyglucoside as a 60% aqueous solution, sold under the name ORAMIX CG110 by the company Seppic | 15% AM |
| Diurethane of oxyethylenated and oxypropylenated alcohols (C16/C18), sold under the name DAPRAL T212 by the company Akzo | 3% |
| Corn starch, sold under the name C*PLUS 05391 by the company Cevestar | 45% |
| Preserving agent, fragrance | qs |
| Water | qs 100% |
| pH adjusted with NaOH to | 5 |

A white paste which is modellable, sticky, difficult to apply, takes a long time to remove and feels coarse in obtained.

EXAMPLE 2

Shampoo

| | |
|---|---|
| Sodium lauryl ether sulphate containing 2.2 EO, sold under the name EMPICOL ESB 3/FL by the company Albright and Wilson at an AM concentration of 28% | 13% AM |
| Cocoylbetaine | 3% AM |
| Polydimethylsiloxane sold under the name SILBIONE OIL 70 047V500000 by the company Rhône Poulenc | 3% |
| Coconut acid monoisopropanolamide | 4% |
| Expanded microspheres of vinyl chloride/acrylonitrile copolymer containing isobutane, sold under the name EXPANCEL 551 DE 20 | 8% |
| Preserving agent, fragrance | qs |
| Water | qs 100% |
| pH adjusted with NaOH to | 7.5 |

A white paste which is non-sticky, smooth, easily modellable, easy to apply and to remove and feels soft is obtained. The foaming power of this shampoo is comparable with that of known shampoos.

COMPARATIVE EXAMPLE 2

Shampoo

| | |
|---|---|
| Oxyethylenated lauryl alcohol mono-sulphosuccinate (30 EO), sold under the name REWOPOL SB FA 30 K4 by the company Rewo | 3% AM |
| Sodium lauryl ether sulphate containing 2.2 EO, sold under the name EMPICOL ESB 3/FG | 8.4% AM |
| Disodium cocoamphodiacetate | 2% AM |
| Mixture of palm glyceride (200 EO) and coconut glyceride (7 EO) 80/20 as a 70% aqueous suspension, sold under the name REWODERM LIS 80 by the company Rewo | 2.1% |
| Pyrogenous silica of hydrophobic nature, sold under the name AEROSIL R 972 by the company Degussa Silices | 24% |
| Preserving agents, fragrance | qs |
| Water | qs 100% |
| pH adjusted with HCl to | 7.5 |

A white paste which is slightly gelled, malleable and difficult to apply and to remove is obtained. The paste feels coarse.

EXAMPLE 3

Shampoo

| | |
|---|---|
| Sodium lauryl ether sulphate containing 2.2 EO, sold under the name EMPICOL ESB 3/FG | 11% |
| Cocoylbetaine | 1.8% |
| Coconut acid monoisopropanolamide | 2.3% |
| Microspheres of nylon 6 on arvosil, sold under the name ORGASOL 1002 D Nat. COS. by the company Atochem | 44% |
| Preserving agent, fragrance | qs |

-continued

| | |
|---|---|
| Water | qs 100% |
| pH adjusted with HCl to | 7.5 |

A white paste which is modellable, smooth and easy to apply is obtained. It is easy to rinse out and feels soft.

EXAMPLE 4

Direct Dye Product

| | |
|---|---|
| Lauryl alcohol oxyethylenated with 12 EO | 10% |
| Cellulose derivative | 1.5% |
| EXPANCEL 551 DE 20 | 9% |
| Dyes | 2% |
| Water | qs 100% |
| Citric acid | qs pH 6 |

The paste obtained is solid, smooth on application, and easy to spread and to remove with water. In addition, the paste is less intensely colored than the conventional dye products, while at the same time providing effective dyeing of the hair, thereby making users less fearful.

EXAMPLE 5

Direct Dye Product

| | |
|---|---|
| Lauryl alcohol oxyethylenated with 12 EO | 10% |
| Glass beads (SCOTCHLITE GLASS BUBBLES S 22) | 35% |
| Cellulose derivative | 1.5% |
| Dyes | 2% |
| Water | qs 100% |
| Citric acid | qs pH 6 |

The paste obtained is solid, modellable and easy to remove with water.

EXAMPLE 6

Direct Dyeing

| | |
|---|---|
| Lauryl alcohol oxyethylenated with 12 EO | 10% |
| ORGASOL 2002 U.D. Nat COS (microspheres of Nylon 12) | 42% |
| Cellulose derivative | 1.9% |
| Dyes | 2% |
| Water | qs 100% |
| Citric acid | qs pH 6 |

The paste obtained in solid, modellable and easy to remove with water.

In Examples 4, 5 and 6, the dyes used are dyes conventionally used in direct dyeing, and in particular;

HC Blue 2
HC Red 3
Basic Blue 99.

EXAMPLE 7

Oxidation Dying

| Phase 1 as a paste containing the oxidation dye precursors: | |
|---|---|
| Sodium lauryl sulphate | 20% |
| CARBOPOL (polycarboxyvinyl) | 2% |
| EXPANCEL 551 DE 20 | 9% |
| Dye precursors | 2% |
| Ammonia as an aqueous solution containing 20% of $NH_3$ | 12% |
| Water | qs 100% |

Phase 1 is a soft modellable solid.

| Phase 2, oxidizing paste: | |
|---|---|
| 200-volumes aqueous hydrogen peroxide solution | 12% |
| Self-emulsifying waxes | 2% |
| Stabilizers | 0.6% |
| EXPANCEL 551 DE 20 | 9% |
| Water | qs 100% |
| pH | 2 |

Phase 2 is also a soft modellable solid.

The two pastes are mixed together by hand at the time of use, and the mixture is then applied to wet hair. It is left to act for 20 min and then rinsed out with water. The color is comparable to that conventionally obtained.

EXAMPLE 8

Paste Reducing Agent

A reducing paste for the reshaping of the hair is prepared according to the invention, by mixing the following ingredients;

| | |
|---|---|
| Thioglycolic acid | 10% |
| Sequestering agent | 0.2% |
| Coconut fatty acid amidopropylbetaine | 1.3% |
| EXPANCEL 551 DE 50 | 6% |
| Fragrance | 0.5% |
| Aqueous ammonia | qs pH = 9 |
| Demineralized water | qs 100% |

This composition is applied with a brush to wet hair which has been wound beforehand on rollers. It is left to act for 15 min and then rinsed out thoroughly with water.

The following oxidizing composition is then applied:

| | |
|---|---|
| 200-volumes aqueous hydrogen peroxide solution | qs 4.8 g |
| Stabilizers | 0.006 g |
| Oleyl alcohol containing 20 mol of ethylene oxide | 1.5% AM |
| Citric acid | qs pH = 3 |
| Demineralized water | qs 100% |

The oxidizing composition is left to act for 10 min. It is rinsed out with water and the rollers are then removed. After drying, it is observed that the hair has beautiful curls with a good degree of curliness. No "running" of the reducing agent is observed during application of the paste reducing agent, and less of an odor is noticed during the reduction phase.

A considerable decrease in the unpleasant odor relative to conventional permanent-waving compositions is also noted.

EXAMPLE 9

Paste Reducing Agent

This example is performed in the same way as Example 8, except that the following reducing paste is used:

| | |
|---|---|
| Thioglycolic acid | 9% |
| Sequestering agent | 0.2% |
| Coconut fatty acid amidopropylbetaine | 1.3% |
| SCOTCHLITE GLASS BUBBLES S 22 (product from the company 3M) | 30% |
| Fragrance | 0.5% |
| Ammonium bicarbonate | 3% |
| Aqueous ammonia | qs pH = 8.5 |
| Demineralized water | qs 100% |

EXAMPLE 10

Paste Fixing Agent

After applying the paste reducing agent according to the same compositions as in Examples 8 and 9 and the same procedure as in these Examples 8 and 9, the following composition is applied with a brush:

| | |
|---|---|
| 200-volumes aqueous hydrogen peroxide solution | 4.8 g |
| Stabilizers | 0.06% |
| Oleocetyldimethylammonium chloride | 1.7% |
| EXPANCEL 551 DE 50 | 6.0% |
| Citric acid | qs pH = 3 |
| Demineralized water | qs 100% |

The composition is left to act for 10 min. It is rinsed out with water and the rollers are then removed. The same type of result as above is obtained.

EXAMPLE 11

Conditioner

| | |
|---|---|
| Behenyltrimethylammonium chloride at a concentration of 80% in a water/isopropanol mixture (15/85) | 1% |
| DC 929 cationic emulsion (iron: Dow Corning) | 4% |
| Chlorhexidine hydrochloride | 0.02% |
| Methyl p-hydroxybenzoate | 0.2% |
| EXPANCEL 551 DE 50 | 8% |
| Sterilized demineralized water | qs 100% |

Procedure: The conditioner is applied to wet hair. it is left in place for 2 minutes and then rinsed out. It is very easy to remove and the disentangling of the hair is very good. Once dried, the hair is very soft and shiny.

Obviously, numerous modifications and variations of the present invention are possible in light of the above teachings. It is therefore to be understood that within the scope of the appended claims, the invention may be practiced otherwise than as specifically described herein.

This specification is based on French patent application FR 94-08567, filed with the French Patent Office on Jul. 11, 1994, the entire contents of which are hereby incorporated by reference.

What is claimed as new and is desired to be secured by Letters Patent of the United States is:

1. A hair composition, comprising, in a cosmetically acceptable medium, i) an active agent; and ii) a structuring agent insoluble in said medium and formed of solid particles, in an effective amount which imparts a deformable solid appearance to said hair composition in which said medium is contained, said structuring agent being capable of being removed from hair using a diluent.

2. The composition of claim 1, wherein said structuring agent has a density of less than 0.09 kg/cm$^3$.

3. The composition of claim 1, wherein said structuring agent has a density of less than 0.04 kg/cm$^3$.

4. The composition of claim 1, wherein said particles are made of a thermoplastic material.

5. The composition of claim 1, wherein said particles are made of a material selected from the group consisting of glass, polymers and copolymers of vinylidene chloride, or acrylonitrile and/or of an acrylic or styrene monomer, nylon and a mixture thereof.

6. The composition of claim 1, wherein said particles are particles of a copolymer of vinylidene chloride, of acrylonitrile and/or of an acrylic or styrene monomer, which is expanded.

7. The composition of claim 1, wherein said particles are present in an amount at least greater than the critical pigment charge volume.

8. The composition of claim 1, wherein said composition further comprises at least one active agent selected from the group consisting of detergents, dyes, permanent-waving agents, polymers, cations and a mixture thereof.

9. A process for treating keratin fibers, comprising applying a composition according to claim 1 to keratin fibers and then in rinsing said fibers.

10. A process for dyeing, bleaching, permanent-waving, washing and/or conditioning keratin fibers, comprising applying a composition according to claim 1 to keratin fibers and then in rinsing said fibers.

11. A process for delivering an active agent onto keratin fibers, comprising i) enclosing an active agent in a deformable solid containing a cosmetically acceptable medium and a structuring agent insoluble in said medium, formed of particles; ii) applying at least some of said deformable solid to keratin fibers, in the presence of water, in order to release the active agent in it; and iii) removing said structuring agent by rinsing said fibers.

12. The process of claim 11, wherein said structuring agent has a density of less than 0.9 kg/cm$^3$.

13. The process of claim 11, wherein said particles are made of a material selected from the group consisting of glass, polymers and copolymers of vinylidene chloride, and nylon.

14. The process of claim 11, wherein said particles are hollow particles based on expanded poly(vinylidene chloride).

15. The process of claim 11, wherein said active agent is selected from the group consisting of detergents, dyes and permanent-waving agents.

16. The composition of claim 1, wherein an amount of said particles in the composition is equal to or greater than the critical pigment charge volume.

17. The process of claim 11, wherein an amount of said particles in said deformable solid is equal to or greater than the critical pigment charge volume.

* * * * *